United States Patent [19]

Rosevear

[11] 4,452,892

[45] Jun. 5, 1984

[54] IMMOBILIZATION OF BIOLOGICALLY ACTIVE MATERIAL IN A HYDROGEL ON A SUPPORT

[75] Inventor: Alan Rosevear, Uffington, England

[73] Assignee: United Kingdom Atomic Energy Authority, Great Britain

[21] Appl. No.: 299,862

[22] Filed: Sep. 3, 1981

[30] Foreign Application Priority Data

Sep. 11, 1980 [GB] United Kingdom ................. 8029343

[51] Int. Cl.³ ...................... C12N 11/14; C12N 11/10; C12N 11/12; C12N 11/04
[52] U.S. Cl. .................................... 435/176; 435/178; 435/179; 435/180; 435/182
[58] Field of Search ............... 435/174, 176, 177, 178, 435/179, 180, 181, 182

[56] References Cited

U.S. PATENT DOCUMENTS

| | | | |
|---|---|---|---|
| 3,809,613 | 5/1974 | Vieth et al. ...................... | 435/177 X |
| 3,849,253 | 11/1974 | Harvey et al. ...................... | 435/182 |
| 3,860,490 | 1/1975 | Guttag .................................. | 435/182 |
| 4,004,979 | 1/1977 | Arrameas et al. ............... | 435/181 X |
| 4,148,689 | 4/1979 | Hino et al. ........................ | 435/182 |
| 4,269,941 | 5/1981 | Ichimura ........................... | 435/182 |
| 4,323,650 | 4/1982 | Rosevear ......................... | 435/182 X |
| 4,335,017 | 6/1982 | Miles et al. ...................... | 435/181 X |
| 4,336,161 | 6/1982 | Rosevear et al. ............... | 435/181 X |
| 4,338,401 | 7/1982 | Cremonesi ....................... | 435/182 X |

*Primary Examiner*—David M. Naff
*Attorney, Agent, or Firm*—Larson and Taylor

[57] ABSTRACT

Biologically active material is immobilized by forming a gel precursor containing the biologically active material, a polymerizable material and a viscosity enhancing agent, applying the gel precursor to a support material and gelling the gel precursor by polymerization to form a hydrogel containing the biologically active material on the support material. A least some of the hydrogel is enmeshed with the support material. By use of the viscosity enhancing agent, the gel precursor is provided with preferred rheological properties.

7 Claims, No Drawings

IMMOBILIZATION OF BIOLOGICALLY ACTIVE MATERIAL IN A HYDROGEL ON A SUPPORT

The present invention relates to composite materials and more particularly to composite materials containing immobilized biologically active species and the preparation and use thereof.

U.S. Pat. No. 3,922,432, discloses, inter alia:

"A thin layer medium for use in chromatographic or electrophoretic processes or radioimmunoassy procedures, said medium comprising an exposed surface layer of discrete particles of solid material containing sorbed water, said particles being of a size on No. 18 screen U.S. Standard Sieve Series, said particles being bonded to a sheet of hydrated gel material, said sheet being a continuous layer formed by the gelling of an aqueous solution of gelling agent".

The said U.S. Pat. No. 3,922,432 also dicloses:

"A medium for use in chromatographic or electrophoretic processes or radioimmunnoassay procedures, said medium comprising an exposed surface layer of discrete particles of solid material containing sorbed water, said particles being of a size to pass a No. 18 screen U.S. Standard Sieve Series, said particles being dispersed in a sheet of hydrated gel material, said sheet being a continuous layer formed by the gelling of an aqueous solution of gelling agent, said sheet being scored to expose the surfaces of said particles".

The scoring may be effected with, for example, a scalpel and it is disclosed that, optionally, the sheet may be bonded to a support member such as glass or polyethylene terephthalate. It is further disclosed that the particles may contain sorbed or dispersed therein, for example antigens, enzymes or substrates.

In accordance with the present invention a particulate biologically active species is not "exposed" but is protected in a permeable gel which is enmeshed with a support material and thus any tendency for the active species to be lost by attrition which would be encountered with exposed active species is substantially avoided. Furthermore, the permeable gel in accordance with the present invention is not scored nor cut to expose the active species and thus any weakness in the permeable gel which would be introduced by scoring or cutting is substantially avoided.

British Patent Specification No. 1556584 discloses, inter alia a process for producing a hydrophilic complex gel. The complex gel is produced by mixing an aqueous solution of a water-soluble polymer with a tetraalkoxysilane of the general formula $Si(OR)_4$ (wherein R is an alkyl group containing up to 12 carbon atoms), hydrolysing the mixture at a pH below 3 with an acidic compound to give a homogeneous complex sol and gelling the sol to form hydrophilic complex gel. Microbial cells may be dispersed in the sol prior to gelling.

In accordance with the present invention a composite material containing particulate biologically active species includes a support material to provide, inter alia, dimensional stability.

According to one aspect of the present invention there is provided a method for the preparation of a composite material containing an immobilized biologically active species which comprises applying a gel precursor to a support material, the said gel precursor containing a particulate biologically active species and gelling the gel precursor to form a composite material comprising the support material, a permeable gel retained on the support material, at least some of the gel being enmeshed with the support material, and, immobilized in the gel, the particulate biologically active species, the rheological properties of the gel precursor being selected (i) to facilitate application of the gel precursor to the support material and (ii) to facilitate retention of the gel precursor on the support material prior to and during the gelling and/or to inhibit the sedimentation of biologically active species prior to, and during gelling.

The gel precursor can for example contain the particulate biologically active species and a gel forming material which can be gelled after application to the support material thereby to form a gel in which the particulate biologically active species is immobilized.

The rheological properties of the gel precursor can optionally be controlled by the addition thereto of a viscosity enhancing agent.

The particulate biologically active species may be as for example cells, sub-cellular particles, substantially non-soluble enzyme complexes and particles containing immobilized enzymes, proteins or nucleic acids.

Optionally more than one particulate biologically active species may be immobilized in the permeable gel.

The gel precursor can be formed by suspending particulate biologically active species in a gel forming material, and/or a viscosity enhancing agent.

Where a gel precursor is prepared in accordance with the present invention by mixing a particulate biologically active species with a gel forming material and/or a viscosity enhancing agent it is preferred that the particulate biologically active species is added to the gel forming material and/or the viscosity enhancing agent immediately prior to application to the support material. In this way the biologically active species is exposed to adverse conditions for as short a time as possible.

The term "particulate biologically active species" as used in this specification embraces, inter alia, viable and non-viable whole cells, viable and non-viable sub-cellular particles which are biologically active and proteinaceous substances (e.g. enzymes, enzyme complexes, proteins, glyco-proteins and nucleic acids) which are insoluble or are immobilized in particles. Furthermore it is to be understood that the term "biologically active species" embraces, inter alia, those substances capable of participating in biologically specific interactions, such substances including, for example, substances of biological origin and those which act on living organisms. Substances of synthetic origin which can participate in reactions involving specific biological interactions analogous to those which can occur with naturally occuring substances are also embraced within the term "biologically active species".

The gel forming material, if used, and viscosity enhancing agent, if used, should be such that there is no adverse interaction with either the particulate biologically active species, the support material, nor any substantial disruption of the gel structure as a result of any permanent grafting of the gel to the viscosity enhancing agent. Similarly the gel formed by gelling the gel precursor should be such that it does not adversely interact with the support material nor with fluids and biochemical species with which it comes into contact in use.

The gel can be any stable gel which is: (i) capable of being retained on the support material, (ii) capable of retaining the particulate biologically active species to immobilize it and (iii) permeable (i.e. capable of permitting species for participation in biochemical reactions to migrate through to reach the immobilized biologically active species to react therewith).

In the case of a composite material to be used in aqueous media the gel is preferably a hydrogel. The choice of support material and the rheological properties (e.g. consistency and physical properties such as viscosity) of the gel precursor may, for example, be such that the gel precursor can be spread onto a support material and such that substantially none of the gel precursor applied to the support material leaves the support material prior to and during the gelling of the precursor.

By way of further example, lower viscosity gel precursors can be used in connection with a mould which retains the gel precursor in contact with the support material during gelling. Such lower viscosity gel precursors can have rheological properties such as to inhibit the settling out (i.e. sedimentation) of the particulate biologically active species prior to and during gelling. This can be particularly important with certain particulate biologically active species such as particles carrying immobilized enzymes and large cells such as plant cells.

The support material which is to provide dimensional stability to the composite material can be any suitable two- or three-dimensionally stable material capable of retaining the gel.

Examples of "two-dimensionally" stable materials are nylon mesh, steel mesh and woven materials such as loosely woven cloth (e.g. that available under the trade name "J-cloth" from Johnson and Johnson Ltd.). In the cases of meshes and loosely woven cloth the gel can be enmeshed with the support in the sense that some of the gel precursor will have passed through holes of the mesh or cloth weave with the result that, after gelling, there is gel on both sides of the mesh or cloth so that the support material is encased by, and enmeshed with, the gel. The support material thereby acts to "reinforce" the gel. In the case of using a mesh or cloth the thickness of the gel is preferably not greater than that which can be protected by the mesh or cloth (e.g. typically not more than 3 mm away from the face of the mesh or cloth). Where the gel is to be retained predominantly on the surface of the support material it is preferred that the surface of the support material is either rough, irregular, porous or otherwise capable of allowing the gel to "key" to it.

Examples of three-dimensionally stable support materials are porous materials such as porous particles made by a method as disclosed in British Patent No. 1421 531 (UKAEA).

Other examples of support materials are thin section sponges, roughened metal plates and ceramic surfaces.

It will be appreciated that in the case of a porous support material (e.g. porous particles) with inter-connected internal porosity, it can be arranged if desired, that the majority of gel containing the particulate biologically active species is present within the pores of the porous support material rather than on the surface thereof.

Thus it is to be understood that in this context "retained on the support material" is used in this specification to embrace also "retained in the support material".

Where the gel is to be retained on the support material predominantly by being in the pores of the support material the gel precursor containing biologically active species may be applied to the support material in a volume sufficient just to fill the pore volume.

After gelling it is preferred to wash away any loosely bound gel prior to using the composite material for effecting biochemical reactions. Thus, for example, in the case of a composite suitable for use in a packed bed reactor and comprising porous particles with gel containing particulate biologically active species in the pores of the particles it is preferred to remove gel which is not stably enmeshed within the particles. It will be appreciated that this is to remove loose, non-rigid gel from between the particles and thereby inhibit the tendency of a bed to compress in use.

The gelling of the gel precursor can be effected in a number of ways depending upon the composition thereof.

Thus in one embodiment the gel precursor contains a gel forming material which is a polymerisable material and gelling is then effected by polymerising said polymerisable material.

For example, gelling may be effected by forming a homo-polymer within the gel precursor thereby to give a gel. By way of example predominately homo-polymeric gels can be formed by radical initiation of monomers such as acrylic or vinyl monomers. The monomer is preferably water soluble (e.g. acrylamide, hydroxyethlmetharylate, acrylic acid, high molecular weight diacrylates and methacrylates or mixtures of these) or can be maintained in a micro emulsion (e.g. acrylonitrile).

To assist in providing good gel strength it is usually preferred to include a di-functional compound as a minor component in the monomer mixture. Such di-functional compounds can be acrylics such as NN'-methylene-bis-acrylamide or glyoxyl-bis-acrylamide.

Radicals may be generated for example by use of persulphate, peroxide, radiation (ultra violet or gamma) or transition metal ions.

In another embodiment where the gel precursor also contains a viscosity enhancing agent gelling of the precursor can be effected, for example, by grafting polymer to the viscosity enhancing agent.

Some degree of grafting to the viscosity enhancing agent can be expected in many polymerisation reactions but is likely to be greatest when one electron transfer agent is introduced to the gel precursor. Such electron transfer agents include Fe(II), Ce (IV) and Ti (III).

In a further embodiment gelling of the gel precursor can be effected, for example, by cross-linking the viscosity enhancing agent (when present in the gel precursor).

Certain gel forming materials such as viscous polymers can be gelled directly. Thus for example alginic and polygalacturonic acids can be cross-linked by calcium and maleic anhydride co-polymer can be cross-linked with polyvinyl alcohol. Where viscous gel forming materials which can be directly gelled are used it can be found that it is not necessary to use an additional viscosity enhancing agent providing the gel forming material allows a gel precursor of suitable rheological properties to be prepared at relatively low gel forming material concentrations. It will be understood that the gel forming material itself is acting as a viscosity enhancing agent under these circumstances. Thus for example with alginic acid or maleic anhydride no supplementary viscosity enhancing agent is needed.

Where the gel is an organic polymeric gel polymers which form gels with very low solids contents (i.e. less than 10% weight per volume) are preferred since this gives a high porosity to the gel and facilitates access of species for participating in biochemical reactions to the immobilised particulate biologically active species.

In one embodiment the gel precursor can contain a solution of an organic polymeric material at a temperature above ambient which is capable of setting to a gel on cooling. An example of such a material is agar solution which can be heated to enable it to be spread onto a support material and subsequently cooled to give a rigid gel.

It has been found that an aqueous solution of agar (at approximately 2½% weight per volume) which sets on cooling to form a stable gel is convenient for forming a composite material in accordance with the present invention.

In accordance with one embodiment of the present invention the gel precursor is applied to the support material by spreading the gel precursor thereon. The spreading may be effected, for example, with the aid of a brush.

As hereinbefore stated the rheological properties of the gel precursor can be controlled, inter alia, by the use of a viscosity enhancing agent. (This is discussed in more detail hereinafter).

For example the viscosity of a given gel precursor can be made sufficiently high for effecting application by spreading to a support material in accordance with the present invention by incorporation of a viscosity enhancing agent.

Thus where the gel precursor containing biologically active species is to be applied by spreading (e.g. with the aid of a paint brush, glass rod, or plate spreader) onto a support material the gel precursor is controlled to have a viscosity which whilst permitting application is also sufficiently high to enable the applied gel precursor containing the biologically active species to remain on the support material during the subsequent gelling operation.

Similarly where the gel precursor containing the particulate biologically active species is introduced into the pores of the support material prior to gelling the rheological properties are selected to permit entry of the gel precursor into the pores.

The viscosity enhancing agent should be compatible with the particulate biologically active species (i.e. should not inhibit nor inactive the biologically active species nor be attacked by it during gelling of the gel precursor) and also the viscosity enhancing agent should not inhibit gelling particularly when gelling is effected by polymerization.

It has been found that gel precursors with a viscosity of approximately 1000 cp are convenient for spreading onto horizontal or sloping surfaces. However the rheological properties of a gel precursor can be chosen to suit a particular circumstance. Thus, for example, gel precursors having viscosities between a 100 and 10,000 cp can be useful in carrying out the method of the present invention where the gel precursor is applied to a support material by spreading thereon.

It will be appreciated that where the gel precursor is to be applied by spreading on a support material viscosity is preferably such that the gel precursor is sufficiently fluid to be spread evenly on the surface but sufficiently viscous to remain as a coating during subsequent treatment to effect gelling.

The following aqueous solutions and hydro-colloid suspensions are examples of substances suitable for use as viscosity enhancing agents in accordance with the present invention:

Xanthan gum (1%)
Sodium alginate (2½%)
Carboxymethyl cellulose-sodium salt (3%)
Cellulose ethers (2%) (e.g. "Cellacol" produced by British Celanese, Derby)
Polyvinyl alcohol (10%)
Agarose (2½%)
Cold water soluable starch (sold under the name LAP) (5%)
Cellulose paste (sold under the name Polycel) (5%)
Carrageenam (3%)

The above concentrations may need minor adjustments depending upon the nature of the particulate biologically active species. Other non-toxic viscous substances may be used as viscosity enhancing agents for example acrylic acid, polymers and co-polymers, pectins and other non-toxic polymers.

In one embodiment of the method of the present invention a sheet of composite material containing an immobilized particulate biologically active species is prepared by pouring a gel precursor onto a horizontally stretched cloth or mesh, spreading the gel precursor substantially evenly over the cloth or mesh and thereafter treating the gel precursor on the cloth or mesh to form a gel.

The cloth or mesh carrying the gel precursor may be treated to form a gel by floating the cloth or mesh carrying the gel precursor in a reagent capable of gelling the gel precursor.

In another embodiment a sheet of composite material containing an immobilized particulate biologically active species is prepared by spreading a gel precursor containing a particulate biologically active species, a gel forming material and an inactivated gelling initiator onto a horizontally stretched cloth or mesh and subsequently activating the gelling initiator thereby to form a gel from the gel precursor.

By way of example the cloth carrying the gel precursor may be placed on a smooth surface and the inactivated gelling initiator activated to form a gel. Activation of the gelling initiator can be, for example, by irradiation or by removing oxygen (e.g. by means of vacuum or purging with an inert gas such as nitrogen).

In a further embodiment the support material may be held between two glass plates separated by a rubber (e.g. silicone) gasket and the gel precursor poured into the remaining space and subsequently gelled.

In the case of lower viscosity gel precursors where the rheological properties are chosen primarily to inhibit the tendency of particulate biologically active species to settle out prior to and during gelling the vicosity enhancing agent when used can be chosen just to keep particles suspended prior to and during gelling without making the gel precursor capable of being spread and retained on a support material.

For example a 0.03% xanthan gum solution is sufficient to give a viscosity in the range (2 cp–10 cp) to inhibit tissue cultured plant cells from settling out of the gel precursor. Similar concentrations of the other visocity enhancing agents hereinbefore mentioned can be used to give a visocity in the same region (2 cp–10 cp). The size and density of the particles of biologically active species must, of course, be taken into account in choosing the rheological properties.

A sheet of composite material prepared in accordance with the present invention may be used in its flat form to effect biochemical reactions.

Alternatively a sheet of composite material prepared in accordance with the present invention can be wound co-axially to give a cylindrical module for use in biochemical processes.

It will be appreciated that a sheet of composite material when wound co-axially gives a "swiss roll" configuration.

It is preferred that an inert spacer is provided between adjacent gel surfaces to provide adequate lumen.

In case of the co-axially wound configuration this may be achieved by rolling a sheet of composite material and a sheet of inert material together to give a substantially cylindrical "swiss roll" configuration in which radially adjacent gel surfaces are separated by the inert material.

Composite materials may be prepared in filamentatious form in accordance with the present invention and tied together so as to pack co-axially in a column.

According to a further aspect of the present invention there is provided a method for effecting a biochemical reaction which comprises contacting a fluid containing species for participation in a biochemical reaction with a composite material wherein the composite material comprises a support material, a gel retained on the support material and, immobilized in the gel a particulate biologically active species.

According to yet a further aspect of the present invention there is provided a method for effecting a biochemical action which comprises contacting a fluid containing species for participation in a biochemical reaction with a composite material prepared by a method in accordance with the present invention.

The invention also provides a composite material prepared by a method in accordance with the invention.

Whilst it is known that soluble enzymes can be immobilized on supports, difficulties can arise in seeking to produce materials containing particulate biologically active species with a support material. Thus, for example, there can be difficulties due to the tendency of the particulate biologically active species to sediment prior to, and during, gelling. In accordance with the present invention sedimentation difficulties may be substantially avoided or overcome.

It is also to be noted that in accordance with the present invention the gelling of the gel precursor can be carried out under mild conditions without wide variations in pH. This can be particularly important when it is desired to prepare a composite material containing a sensitive biologically active species (e.g. eukaryotic cells).

The invention will now be further described by way of example only as follows:

EXAMPLE 1

Xanthan gum (Sigma, 4% suspension in water, 2.5 g) was mixed with 2M TRIS/HCl buffer (pH 8.5, 2.5 ml) and a solution of 20% acrylamide/1% NN-methylene bis acrylamide (5 ml) to give an homogeneous paste. Nitrogen gas was bubbled through the mixture for 3 minutes and then NNNN-tetramethyl 1,2 diaminoethane (TEMED, 0.025 ml) added. Finally a suspension of yeast cells (Sigma-YSC, 0.13g dry weight in 0.5 ml water) was added with mixing to the paste and the gel precursor paste thereby formed was poured onto a square of J-cloth (Johnson and Johnson, 12×12 cm) held horizontally between two clips. The gel precursor paste was spread evenly on the cloth using a paint brush and the resulting coated cloth was subsequently placed into a dish containing 0.2% ammonium sulphate in de-aerated water (50 ml). After 15 minutes, gelling of the gel precursor was complete, and the sheet of composite material was removed, washed several times in distilled water and pre-incubated in sterile 5% glucose solution at 35°. It was then transferred to a solution of fresh, sterile glucose solution (5%, 30 mls) and incubated at 35° for 18 hours. The clear supernatant was then assayed for both glucose and alcohol using proprietary kits supplied by the Boehringer Corporation. The results are given in the Table.

EXAMPLE 2

Yeast cells (Sigma-YSC, 1 g) were suspended in 3% w/v sodium carboxymethyl-cellulose (10 ml). Hydrated ferrous sulphate (0.5 g), glyoxal bis acrylamide, (0.15 g) and hydroxyethylmethacrylate (1.5 ml) were added and the resulting gel precursor was spread onto a nylon sieve mesh (400μ, 7×3 cm) by brush. The resulting coated mesh was laid into a dilute solution of hydrogen peroxide (0.25 ml of 100 volume in 50 ml water) for 15 minutes to initiate polymerisation and thereby effect gelling of the gel precursor to give a sheet of composite material which was then washed and assayed as in Example 1. The composite material had a permanent brown tinge. Assay was carried out as in Example 1 and results are given in the Table.

EXAMPLE 3

Yeast cells (Sigma-YSC, 1 g) were suspended in 1% xanthan gum (Sigma, 10 ml). Glyoxal bis acrylamide (0.15 g) and hydroxyethylmethacrylate (1.5 ml) were added to the resulting paste and the gel precursor paste thereby formed was smeared onto nylon mesh (400μ, 7×3 cm). The resulting coated mesh was laid into a solution of cerium ammonium nitrate (0.01M, 50 ml) which had been saturated with nitrogen. After 2 hours a strong gel had formed on and around the mesh. The gel was pale yellow even after prolonged washing. The coated mesh was washed and assayed as in Example 1 and results are given in the Table.

EXAMPLE 4

Yeast cells (Allisons Bakers yeast, 1 g) were suspended in 2½% w/v sodium alginate (Sigma, 10 ml) and a part of this resulting gel precursor paste was smeared onto nylon mesh (400μ, 7×3 cm) to give an even covering. The resulting coated mesh was then laid into a 5% w/v solution of calcium chloride to gel the gel precursor coating. The resulting sheet of composite material was rolled with a section of stainless steel mesh of similar dimension to give a rigid "swiss roll" cylindrical module in which the stainless steel mesh separated adjacent gel surfaces. The module was packed into a glass column and then eluted with calcium chloride solution and subsequently with 20% w/v glucose solution. The activity of the cells in the composite material was then measured by re-circulating 10 ml of 20% w/v glucose solution through the column for one hour at 20°. The column was then washed with calcium chloride solution and the assay repeated one and six days later. The concentration of ethanol produced on each occasion was 0.3, 0.8 and 0.3 mg/ml respectively.

EXAMPLE 5

Yeast cells (Allisons Bread type, 1 g) was suspended in 0.5% aqueous sodium alginate (Sigma, 3 ml) to give a viscous solution which was then soaked into fabricated kieselguhr particles (400–700µ) made by the method disclosed in BP 1421531 (UKAEA). The volume of the solution used was just sufficient to fill pores of the particles. The filled particles were then dropped into an aqueous solution of calcium chloride (5% w/v) to form a gel within and around the pores. After washing the particles were assayed as in Example 4 giving ethanol values of 1.08, 1.35 and 0.83 mg/ml in the three runs.

EXAMPLE 6

Polygalacturonic acid (0.5 g) was dissolved in 10 ml water by adding a few drops of concentrated caustic soda solution. 4% xanthan gum (2.5 g) was added, followed by 2 ml water and 0.5 ml of a suspension of yeast cells (Sigma YSC.13 g). After mixing, the resulting gel precursor paste was spread evenly on a 12×12 cm square of J-cloth, and the coated cloth was laid into a bath containing 5% w/v calcium chloride to effect gelation of the gel precursor. After washing the composite was assayed as in Example 1 and results are given in the Table.

EXAMPLE 7

Xanthan gum (4% w/v, 2.5 g) and 2M TRIS-HCl buffer (pH 7,2.5 ml) were mixed with 5 ml of 20% w/v acrylamide/1% NN-methylene-bis acrylamide and a suspension of yeast cells (Sigma YSC 0.13 g in 0.5 ml) added. A 5% solution of TEMED (0.1 ml) and 5% ammonium persulphate (0.5 ml) were quickly added, the resulting gel precursor paste was spread onto a 12×12 cm cm square of J-cloth which was then placed in a vacuum dessicator for 25 minutes to gel the gel precursor. The resulting sheet of composite material was washed and assayed as in Example 1. Results are given in the Table.

EXAMPLE 8

Xanthan gum (4% w/v, 2.5 g) and 2M TRIS/HCl buffer (pH 7, 2.5 ml) were mixed with 5 ml of 20% acrylamide/1% NN-methylene-bis acrylamide. A yeast cell suspension (Sigma YSC, 0.13 g in 0.5 ml) 1% ascrobic acid (0.2 ml) and 2% ammonium persulphate (0.2 ml) were added and the resulting gel precursor paste was spread onto a 12×12 cm square of J-cloth. The resulting coated cloth was placed in a vacuum dessicator for 40 minutes to gel the gel precursor and the resulting sheet of composite material was washed and assayed as in Example 1. Results are presented in the Table.

EXAMPLE 9

Xanthan gum (4% w/v, 2.5 g) and 2M acetate buffer (pH 5, 2.5 ml) were mixed with 5 ml of 20% acrylamide/1% NN-methylene-bis acrylamide and riboflavin solution (40 mg/100 ml; 1 ml). A yeast cell suspension (Sigma YSC, 0.3 g in 0.5 ml) was added, the resulting gel precursor paste was spread on a 12×12 cm square of J-cloth and the resulting coated cloth laid between two glass plates in an atmosphere of nitrogen gas. Each side of the coated cloth was irradiated with soft UV light for 7 minutes to gel the gel precursor and form a sheet of composite material which was then washed and assayed as in Example 1. Results are presented in the Table.

EXAMPLE 10

Yeast (Sigma YSC, 1 g) was suspended in 1% w/v xanthan gum (Sigma, 10 ml), hydrated ferrous sulphate (0.5 g), hydroxyethylmethacrylate (1.5 ml) and glyoxal-bis acrylamide (0.15 g) added and the resulting gel precursor paste was smeared onto nylon mesh (400µ, 7×10 cm). The resulting coated mesh was rolled with aluminium foil (8×12 cm) in a glass tube and irradiated with 10K Rads of γ-rays to gel the gel precursor. The gel stuck firmly to the mesh but not to the foil which acted as an inert spacer. The composite material produced was washed and was shown to cause fermentation of glucose solutions.

EXAMPLE 11

Aminoethyl cellulose (0.5 g), Gantrez 139 (a maleic anhydride co-polymer made by GAF Ltd., 1 g) and yeast cells (Sigma YSC, 0.13 g in 0.5 ml) were suspended in 13% polyvinyl alcohol solution (Sigma type II, 10 ml) and the resulting gel precursor paste was spread on a 12×12 cm square of J-cloth. The resulting coated cloth was laid in a covered petri-dish for 24 hours to allow the gel precursor to gel and was then washed and assayed as in Example 1. Results are presented in the Table.

EXAMPLE 12

Warm 5% agar (Oxoid, 5 g) and 4.5 ml of basic nutrient media were mixed at 50° C. and yeast cells (Sigma YSC, 0.13 g in 0.5 ml) added. The resulting gel precursor paste was quickly smeared on a 12×12cm square of J-cloth and left to set in air for one minute before being washed and assayed as in Example 1. The results are given in the Table.

TABLE
FERMENTATION OF GLUCOSE BY IMMOBILIZED YEAST CELLS

| Example | Glucose loss in 18 h mg/ml | Alcohol production mg/ml |
| --- | --- | --- |
| 1 | 7.7 | 0.3 |
| 2 | 4.3 | N/A |
| 3 | 4.6 | N/A |
| 6 | 12.2 | 1.4 |
| 7 | 9.7 | |
| 8 | 0.8 | |
| 9 | 7.5* | |
| 11 | 15.4 | 0.1 |
| 12 | 7.0 | 1.2 |

*Based on polarimeter reading.

EXAMPLE 13

Sterilized xanthan gum (Sigma) in 0.1M phosphate buffer pH6 (1¾% w/v; 6.7 g) was mixed with sterile filtered 36% w/v acrylamide/0.7% NN-methylene-bis-acrylamide (3.3 ml) in the same buffer and nitrogen was bubbled through for 5 minutes. Freshly filtered tobacco cells (ex-suspension tissue culture; 3 g wet weight) was mixed into the paste followed by TEMED solution (10% w/v; 0.2 ml) and ammonium persulphate solution (10% w/v; 0.2 ml). The paste was spread on a J-cloth (10×15 cm) stretched between two clips using a glass rod to give an even surface. The cloth was then placed in a vacuum dessicator for 15 minutes to achieve gelling and the cloth washed in sterile water and wound co-axially with stainless steel mesh of similar dimensions. This roll was then washed with B5 media containing 2% w/v glucose and no hormones before being incubated for 42 hours in 20 ml of this media with aeration. Glucose utilisation was 5.8 mg/ml after this period.

EXAMPLE 14

10% acrylamide 0.25% NN'-methylene-bis-acrylamide and 0.03% xanthan gum in 0.1M phosphate buffer pH6 (10 ml) was sterile filtered and purged with nitrogen gas for 5 minutes. Freshly filtered tobacco cells (3 g wet weight) were added along with ascorbic acid solution (10% w/v 0.6 ml) and ammonium persulphate solution (10% w/v; 0.6 ml). The mixture was poured under nitrogen onto a J-cloth (9×10 cm) held between two glass plates separated by a 1/16" silicone rubber gasket. After 15 minutes the gel sheet composite was removed and assayed as in Example 13. The glucose utilisation over 42 hours was 3.9 mg/ml.

EXAMPLE 15

10% acrylamide 0.25% NN'-methylene-bis-acrylamide and 0.03% xanthan gum in 0.1M phosphate buffer pH6 (10 ml) was sterile filtered and purged with nitrogen for 5 minutes. Freshly filtered Vinca cells (3 g wet weight ex-suspension tissue culture) were added along with TEMED solution (10% w/v; 0.1 ml) and ammonium persulphate solution (10% w/v; 0.1 ml). The mixture was poured under nitrogen onto a J-cloth (9×10 cm) which was held between two glass plates separated by a gasket of silicone rubber of 1/16" thickness. After 15 minutes the gel sheet composite was removed and assayed as in Example 13. The glucose utilisation over 42 hours was 2.6 mg/ml.

EXAMPLE 16

Sterilized sodium alginate solution (3% w/v; 15 g) was mixed with sterile 30% acrylamide (0.75% NN-methylene-bis acrylamide)in 0.1M phosphate buffer pH6 (4.3 ml) and nitrogen bubbled through the mixture for 3 minutes. Freshly filtered Vinca cells (6 g wet weight) were added followed by 10% w/v ammonium persulphate solution (0.4 ml) and 10% w/v TEMED solution (0.4 ml). The suspension was well mixed and poured into a frame formed by two glass plates, separated by a silicone rubber gasket in which was held a section of J-cloth (14½×18 cm). After 15 minutes the gel sheet composite was washed in Gamborg B5 medium containing 0.2% calcium chloride solution (in 100 ml for 15 minutes, then in fresh 100 ml for 1 hour) and incubated in normal medium overnight. These immobilized plant cells were shown to be viable by both respiration and staining techniques based on fluorescein diacetate uptake.

The acrylamide/alginate composite sheets were stable to treatment with calcium complexing agents such as 50 mM methylene diamide tetraacetic acid and 0.4 M phosphate buffer pH6.

EXAMPLE 17

Sterile 30% w/v acrylamide (0.75% NN-methylene-bis acrylamide in 0.1M phosphate buffer pH6 (6.7 ml) was mixed with sterile 0.75% xanthan gum in the same buffer (13.3 g) and nitrogen bubbled through for 3 minutes. Freshly filtered tobacco cells (6 g wet weight) were added followed by 10% w/v ammonium persulphate solution (0.4 ml) and 10% w/v TEMED solution (0.4 ml). The suspension was well mixed, poured into a frame as in Example 16 and left to gel for 15 minutes. The cloth was washed in Gamborg B5 medium and incubated overnight. It was estimated, by staining with fluorescein diacetate, that almost all the plant cells were still viable following immobilization and respired at a high rate.

EXAMPLE 18

White blood cells were washed with physiological saline at 4°, centrifuged and resuspended in a final volume of 20 ml saline. An aliquot (1 ml) at 37° was suspended in a fluid mixture of melted 1.8% sodium alginate/1.1% agarose held at 40°. The resulting mixture was quickly poured into a sterile nylon bag containing J-cloth (5×5 cm). The bag was sealed, placed in a frame to give an even distribution of fluid and allowed to cool slowly to room temperature (~5 minutes) The resulting composite material cloth was washed in physiological saline and the cell viability tested using fluorocein diacetate. The composite material cloth showed good strength properties and the cells in the composite material appeared to have about half the viability of the free cells even after 18 hours in saline.

The gel strength could be improved further by soaking the cloth in 0.2% calcium chloride solution for 5 minutes.

EXAMPLE 19

Mouse myeloma cells capable of producing monoclonal antibodies grown in suspension culture (1.5L), were centrifuged and resuspended in original medium to give a final volume of 20 ml ($2 \times 10^9$ cells/ml). An aliquot (1 ml) of the cells was mixed with 2½% w/v sodium alginate solution (8 g) and 2 ml of human blood plasma and the resulting mixture spread onto a J-cloth (5×5 cm) held on a glass plate. The cloth was then floated into a solution of 0.1% calcium chloride/0.85% saline and gelling allowed to proceed for 5 minutes. The resulting composite material cloth was then washed with physiological saline and incubated in spent growth medium at 37°. The viability of the cells assessed by fluoroscein diacetate assay was 90% 5 hours after preparation of the composite material and 50% 1 day after preparation of the composite material.

I claim:

1. A method for the preparation of a composite material containing an immobilized biologically active species which comprises applying a gel precursor containing a particulate biologically active material to a support material, said gel precursor containing a major amount of a gel forming material selected from the group of monomers consisting of acrylic, acrylate and biacrylate monomers in combination with a minor amount effective to enhance viscosity of a viscosity enhancing agent selected form the group consisting of an aqueous solution or hydrocolloid suspension of xanthan gum, sodium alginate, carboxymethyl cellulose-sodium salt, cellulose ethers, polyvinyl alcohol, agarose, cold water soluble starch, cellulose paste, or carrageenam and gelling the gel precursor by addition and/or condensation radical initiation polymerization to form a hydrogel containing said biologically active material on the support material, the forming of the hydrogel on the support material being such that, after gelling, at least some of the hydro-gel is enmeshed with the support material, and the gel precursor having rheological properties selected (i) to facilitate applying of the gel precursor to the support material and (ii) to facilitate retention of the gel precursor on the support material prior to and during the gelling and/or to inhibit the sedimentation of biologically active materials prior to, and during gelling.

2. A method as claimed in claim 1 wherein the particulate biologically active material comprises cells, sub-cellular material, or a substantially insoluble enzyme.

3. A method as claimed in claim 1 wherein gelling is effected by cross-linking of the gel forming material.

4. A method as claimed in claim 1 wherein the support material comprises material in the form of a mesh, a ceramic material, thin section sponge, or roughened metal plate.

5. A method as claimed in claim 1 wherein the rheological properties of the gel precursor are such that substantially none of the gel precursor applied to the support material leaves the support material prior to and during the gelling of the precursor.

6. A method for effecting a biochemical action which comprises contacting a fluid containing species for participation in a biochemical reaction with a composite material prepared by a method as claimed in claim 1.

7. A method as claimed in claim 1 wherein the particulate biologically active material comprises protein or nucleic acid.

* * * * *